United States Patent [19]
Pfaff et al.

[11] Patent Number: 6,156,115
[45] Date of Patent: Dec. 5, 2000

[54] MULTILAYER INTERFERENCE PIGMENT WITH TRANSPARENT CENTRAL LAYER

[75] Inventors: Gerhard Pfaff, Münster; Gerd Bauer, Klein-Ostheim; Martin Friz, Mühltal; Matthias Kuntz, Seeheim; Christina Schank, Mühltal, all of Germany

[73] Assignee: Merck Patent Gesellschaft mit beschrankter Haftung, Germany

[21] Appl. No.: 09/171,803

[22] PCT Filed: Feb. 18, 1998

[86] PCT No.: PCT/EP98/00930

§ 371 Date: Oct. 26, 1998

§ 102(e) Date: Oct. 26, 1998

[87] PCT Pub. No.: WO98/38254

PCT Pub. Date: Sep. 3, 1998

[30] Foreign Application Priority Data

Feb. 27, 1997 [DE] Germany .................. 197 07 806

[51] Int. Cl.[7] .............. C09C 1/00; C09C 1/04; C09C 1/22; C09C 1/24; C09C 1/36
[52] U.S. Cl. .............. 106/403; 106/400; 106/415; 106/425; 106/436; 106/456
[58] Field of Search .................. 106/403, 426, 106/429, 445, 459, 460, 453, 454, 436, 442

[56] References Cited

U.S. PATENT DOCUMENTS

| | | | |
|---|---|---|---|
| 5,278,694 | 1/1994 | Wheatly et al. | 359/359 |
| 5,281,480 | 1/1994 | Phillips et al. | 428/412 |
| 5,332,618 | 7/1994 | Austin | 428/216 |
| 5,569,535 | 10/1996 | Phillips et al. | 428/403 |

OTHER PUBLICATIONS

English Abstract of EP 0 753 545.

*Primary Examiner*—Mark L. Bell
*Assistant Examiner*—Michael J. DiVerdi
*Attorney, Agent, or Firm*—Millen, White, Zelano, & Branigan, P.C.

[57] ABSTRACT

Multilayer interference pigment consisting of a central layer of a transparent or semitransparent material of low refractive index and alternating layers of a metal or of a material of high refractive index and of a material of low refractive index either side of the central layer, the material of low refractive index preferably being magnesium fluoride or acrylate and the metal preferably being aluminium or chromium.

15 Claims, 2 Drawing Sheets

MULTILAYER INTERFERENCE PIGMENT
WITH TRANSPARENT CENTRAL LAYER

The invention relates to multilayer interference pigments consisting of alternating layers of a material of low refractive index and of a metal or of a material of high refractive index, the central layer being formed from a transparent or semitransparent material of low refractive index.

BACKGROUND OF THE INVENTION

Multilayer pigments having alternating layers of a material of high refractive index and a material of low refractive index are known. They comprise predominantly metal oxides. However, the material of high refractive index can also be replaced by a semitransparent metal layer. The metal oxide layers are produced either by a wet method, by precipitating the metal oxide hydrates from a metal salt solution onto a substrate material, or by vapour deposition or sputtering in a vacuum. For instance, U.S. Pat. No. 4,434,010 describes a multilayer interference pigment consisting of a central layer of a reflective material (aluminium) and alternating layers of two transparent, dielectric materials of high and low refractive index, for example titanium dioxide and silicon dioxide, either side of the central aluminium layer. In a further embodiment of the pigment the layers following the central aluminium layer are formed by magnesium fluoride and chromium. This pigment is employed for the printing of securities.

JP H7-759 (A) describes a multilayer interference pigment with a metallic lustre. It consists of a substrate which is coated with alternating layers of titanium dioxide and silicon dioxide. The substrate is formed from platelets of aluminium, gold or silver, or from platelets of mica and glass which are coated with metals. This pigment has a high hiding power. For applications where high transparency of the pigmented material is required, for example for agricultural films, the pigment is unsuitable. Furthermore, it has the disadvantage that the typical depth effect of interference pigments is not produced, since the high level of reflection of the light at the metal layer which forms the core means that pigment particles lying deeper within the application medium are able to make only a very small contribution to the optical appearance. The interference effect is therefore limited to the layers located on the metal layer.

SUMMARY OF THE INVENTION

The object of the invention is to provide substantially transparent interference pigment having strong interference colours and a close angular dependency of the interference colours. Furthermore, the object of the invention is to provide pigments having special spectral characteristics in the visible range and in the infrared range.

This object is achieved according to the invention by a multilayer interference pigment consisting of a central layer of a transparent or semitransparent material of low refractive index and alternating layers of a metal or of a material of high refractive index and of a material of low refractive index on either side of the central layer.

This object is also achieved, according to the invention, by a process for preparing the novel pigment by applying a release layer comprising a water- or solvent-soluble material to a substrate, depositing a layer system comprising alternating layers of a material of low refractive index and of a metal or of a material of high refractive index onto the release layer, the central layer applied being a layer of a transparent or semitransparent material of low refractive index, removing the layer system formed from the substrate by dissolving the release layer, and washing and drying the resulting platelet-shaped interference pigment, heat-treating the pigment in a stream of nitrogen at from 100 to 300° C., and milling and classifying the treated pigment.

The invention also provides for the use of the novel pigments for pigmenting paints, printing inks, plastics and cosmetics and for producing films.

The material of high refractive index is a metal oxide or mixtures of metal oxides with or without absorbing properties, for example $TiO_2$, $ZrO_2$, $Fe_2O_3$, $Fe_3O_4$, $Cr_2O_3$ or ZnO, or a compound of high refractive index, for example iron titanates, iron oxide hydrates or titanium suboxides or mixtures and/or mixed phases of these compounds with one another or with other metal oxides.

The metal is preferably aluminium, chromium, nickel, a chromium-nickel alloy or silver. Chromium and aluminium are preferred in this context, since they are easy to deposit. Furthermore, the layers here have a reflectivity which is easy to control and high corrosion resistance.

The material of low refractive index is $MgF_2$ or a metal oxide such as $SiO_2$, $Al_2O_3$ or a mixture thereof, and can likewise have absorbing or nonabsorbing properties. If desired, the material of low refractive index can include alkali metal oxides and alkaline earth metal oxides as constituents.

As the material of low refractive index it is preferred to employ polymers, for example acrylates. The monomers used have a molecular weight of from 200 to 1000 and are available as mono-, di- or triacrylates. In terms of functional groups they are available as hydrocarbons, polyols, polyethers, silicones or as fluorinated Teflon-like monomers. These monomers can be polymerized by means of electron beams or UV radiation. The resulting layers possess temperature stability up to 250° C. The refractive indices of the acrylate layers are in the range from 1.35 to 1.60. Further details can be found in David G. Shaw and Marc G. Langlois: Use of a new high speed acrylate deposition process to make novel multilayer structures, MRS Conference in San Francisco in 1995; A new high speed process for vapor depositing fluoro and silicone acrylates for release coating applications, Conference of the Society of Vacuum Coaters in Chicago, Ill. 1995.

The difference in refractive indices between a layer of high refractive index and a layer of low refractive index should be at least 0.1.

The layer thickness of the layers of low and high refractive index is adjusted to values of between 20 nm and 700 nm, preferably between 60 nm and 500 nm. The layer thickness of the metal layers is adjusted to 5 to 20 nm in order to give semitransparency.

The maximum achievable reflection possible with a multilayer system depends on the number of layers and on the refractive indices of the layers:

$$R = \left[ \frac{1 - (n_H/n_L)^{2p} n_H^2}{1 + (n_H/n_L)^{2p} n_H^2} \right]^2$$

In this formula, $n_H$ is the refractive index of the high-index layer, $n_L$ is the refractive index of the low-index layer, and p is the number of layers (layer count). This equation is valid for a layer count of 2p+1.

The layer thickness for maximum reflection is in each case $d = \lambda/4n$ or a multiple thereof with the wavelength $\lambda$. The thickness and number of layers depends on the desired effect in terms of interference colour and angular dependence of the interference colour. $\lambda$ is within the range between 400 nm (violet light) to about 750 nm (red region). In order to obtain appropriate colours, the layer thickness must be adjusted in dependence on the refractive index of the optically thinner medium. In addition, the novel pigments can also be used to produce appropriate pigments which reflect selectively in adjoining wavelength regions (UV—infrared).

In precision optics, for example in the production of mirror layers, beam splitters or filters, layer counts of up to 100 or more are employed. Layer counts of this magnitude are not necessary for the preparation of pigments. The number of layers is normally below 10.

The individual layers are produced in accordance with known techniques by sputtering of metals, for example of aluminium or chromium or of alloys, for example Cr—Ni alloys, and of metal oxides, for example titanium oxide, silicon oxide or indium-tin oxide, or by thermal vaporization of metals, metal oxides or acrylates.

For preparing the novel pigments preference is given to vacuum belt coating, as is described in U.S. Pat. No. 5,440,446 for the production of high-voltage capacitors and in EP 0 733 919 for the production of interference colour filters.

The substrate used for the interference layer system is a flexible strip of polyethylene terephthalate (PET), other polyesters, polyacrylates, polyethylene (PE) or polypropylene (PP).

The release layer which is applied to the substrate in order to enable the interference layer system to be detached from the flexible strip after deposition has taken place consists of a water- or solvent-soluble material, for example polyethylene glycol, wax or silicone. The solvent used is water or acetone.

In the text below, the application of the interference layers by vapour deposition is described in more detail:

In the vapour deposition technique, the substances to be vaporized are heated in a vacuum and vaporized The vapours condense on the cold substrate surfaces, giving the desired thin layers. Vaporization takes place either in metal containers (boats of tungsten, molybdenum or tantalum metal sheet), which are heated directly by passage of a current, or by bombardment with electron beams.

The interference layer system can be prepared using a conventional belt vapour coating unit. The vapour deposition unit consists of the customary components, such as vacuum boiler, vacuum pump system, the pressure meters and control units, vaporizer devices, such as resistance vaporizers (boats) or electron beam vaporizers, a layer thickness measurement and control system, a device for establishing defined pressure conditions, and a gas inlet and regulation system for oxygen.

The high-vacuum vapour deposition technique is described in detail in Vakuum-Beschichtung, Volumes 1–5; Editors Frey, Kienel and Löbl, VDI Verlag 1995.

Application of the layers by the sputtering technique is as follows:

In the case of the sputtering technique or in the case of cathode atomization, a gas discharge (plasma) is ignited between the substrate and coating material (target) which is in the form of plates. The coating material is bombarded with high-energy ions from the plasma, for example argon ions, and is thereby abraded or atomized. The atoms and molecules of the atomized coating material are deposited on the substrate and form the desired thin layer.

Metals or alloys are particularly suitable for sputtering techniques. They can be atomized at comparatively high rates, especially in the so-called DC magnetron process. Compounds such as oxides or suboxides or mixtures of oxides can likewise be atomized using high-frequency sputtering. The chemical composition of the layers is determined by the composition of the coating material (target). However, it can also be influenced by adding substances to the gas which forms the plasma. Oxide or nitride layers, in particular, are produced by addition of oxygen or nitrogen to the gas space.

The structure of the layers can be influenced by means of appropriate measures, such as bombarding the growing layer by ions from the plasma.

The sputtering technique is likewise described in Vakuum-Beschichtung, Volumes 1–5; Editors Frey, Kienel and Löbl, VDI Verlag 1995.

The principle of the application of the layers is described in U.S. Pat. No. 5,440,446 and EP 0 733 919 and is practised as follows:

Referring to FIG. 1, the whole coating unit is located within a conventional vacuum chamber 1. A strip 3 of polyester is wound up on a dispensing roller 2 and already carries a metal layer on one side. Prior to metallization the polyester strip was given a release layer. The polyester strip 3 is guided via a rotating drum 4 and wound up onto the acceptor roller 5. Rollers 6 and 7 serve as tension and guide rollers.

The strip passes through the metallizing station 8, where a semitransparent metal layer is deposited by vacuum vapour deposition or sputtering. The strip then passes through the high-speed vaporizer 9. In the vaporizer there is a gaseous acrylate monomer which is deposited as a thin layer on the metal layer that is located on the substrate strip. The strip then passes through an irradiation station 10 where it is irradiated with electrons or with ultraviolet light. The irradiation initiates the polymerization of the acrylate monomer. The strip subsequently passes through the second metallizing station 11. In station 12 a further acrylate monomer layer is applied, which is polymerized in irradiation station 13 in analogy to the steps which take place in stations 9 and 10. After this, the strip, which is coated with two semitransparent metal layers and two acrylate layers arranged between them, is wound up after passing tension roller 7.

The strip subsequently passes a second time through the vacuum unit, where the metal layers and the acrylate layer are deposited in the same way as during the first pass, although this time stations 12 and 13 are left out of the operation.

For a 7-layer system consisting of a central absorption layer and two metal layers and an acrylate layer on either side of the central layer, two passes through the vacuum coating unit are required.

After the coating operation, the multiple coating is detached by dissolving the release layer in a water bath, possibly at a relatively high temperature, or in a solvent, possibly at a relatively high temperature, by brushing, scraping or, preferably, by rinsing.

Where acrylates are used as the material of low refractive index it is necessary to grind the pigment at relatively low temperatures in the range from 90 to 273 K.

The examples which follow are intended to illustrate the invention.

EXAMPLE 1

Figure 1:
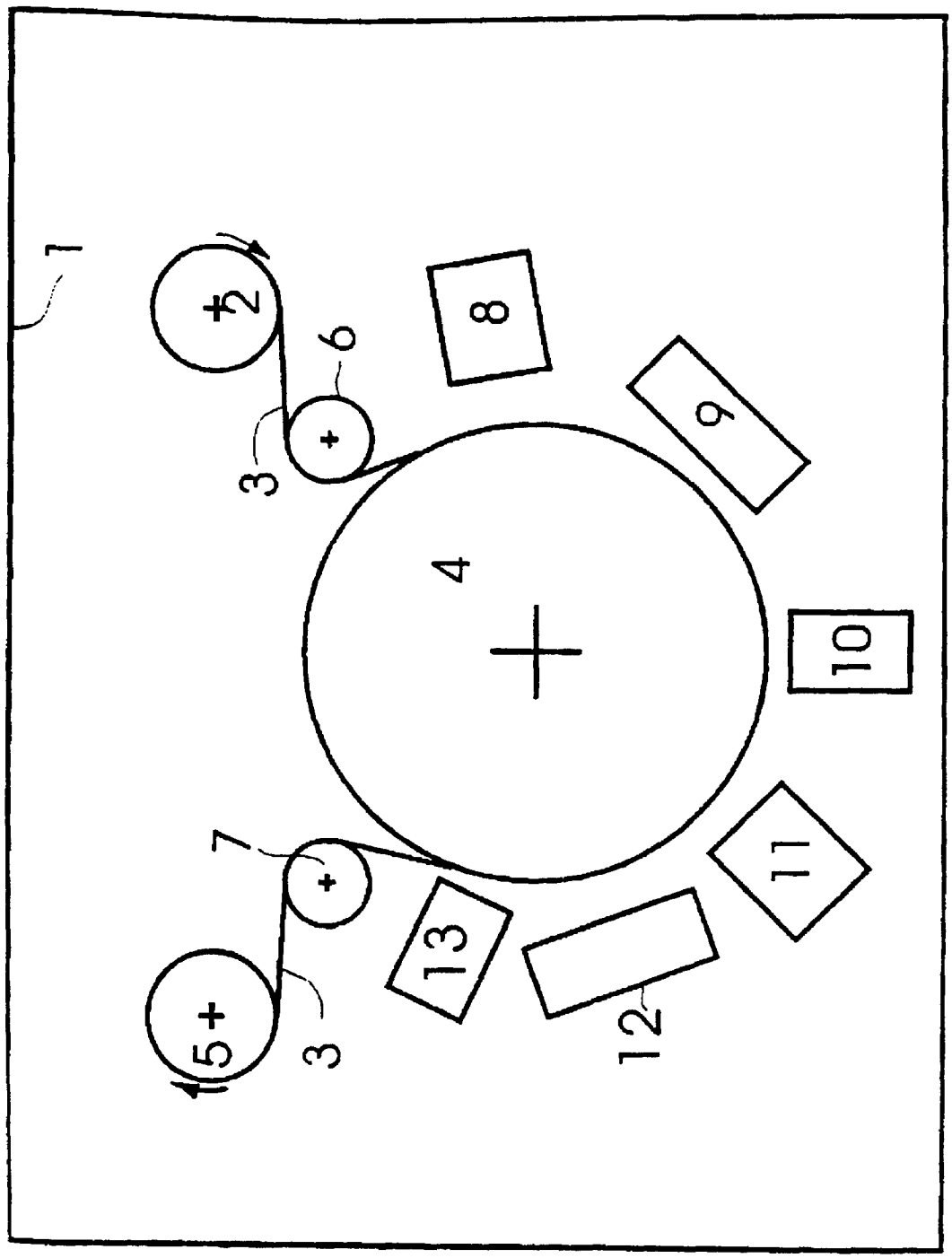
FIG. 1 schematically illustrates an embodiment of a coating unit for the production of a pigment according to the invention.

An interference pigment consisting of 7 layers is produced by alternate vapour deposition of chromium and aluminium and acrylate onto a polyester strip in a vacuum vapour deposition unit in accordance with FIG. 1. The polyester strip is coated with a release layer of stearin. Following the vapour deposition of two chromium and two acrylate layers the strip is sent: a second time through the vacuum unit, where in contrast to the first pass two chromium layers and only one acrylate layer are deposited.

Layer structure of the pigment

| Layer No. | Material | Layer thickness nm |
|---|---|---|
| 1 | chromium | 17 |
| 2 | acrylate | 325 |
| 3 | chromium | 17 |
| 4 | acrylate | 325 |
| 5 | chromium | 17 |
| 6 | acrylate | 325 |
| 7 | chromium | 17 |

The layer system is detached from the substrate strip using acetone, is washed with acetone and is dried. Subsequently the resulting pigment is heated at 300° C. in a stream of nitrogen for 90 minutes and is then comminuted to a mean particle size of 40 μm in a Netsch mortar mill for 30 minutes, mixed with carbon dioxide dry ice, at from −5 to −10° C.

EXAMPLE 2

An interference pigment consisting of 7 layers is produced by alternate vapour deposition of chromium and silver and magnesium fluoride onto a film of polyethylene terephthalate. The film is coated with a release coat of stearin. Vapour deposition is carried out in a high-vacuum deposition unit A 700 Q from the company Leybold AG.

Layer structure of the pigment

| Layer No. | Material | Layer thickness nm |
|---|---|---|
| 1 | Cr | 5 |
| 2 | $MgF_2$ | 453 |
| 3 | Ag | 10 |
| 4 | $MgF_2$ | 90 |
| 5 | Ag | 10 |
| 6 | $MgF_2$ | 453 |
| 7 | Cr | 5 |

Figure 2:
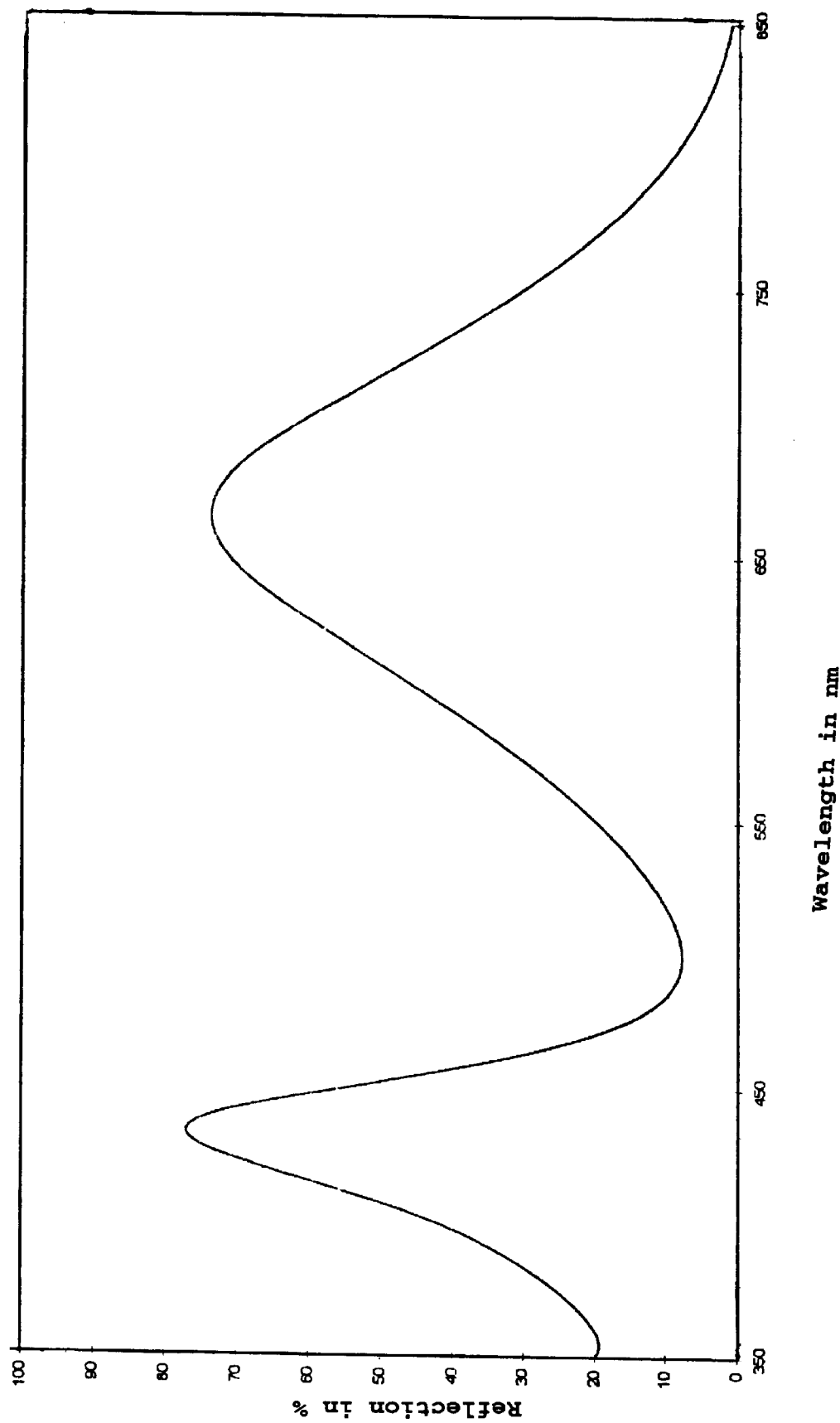
FIG. 2 is a graph illustrating the reflectance values for an embodiment of a pigment of the invention.

The layer system is detached with acetone from the film, is washed with acetone and dried, and is ground in a Netsch mortar mill for 30 minutes. A pigment having a mean particle size of 40 μm is obtained. The reflection spectrum is shown in FIG. 2.

What is claimed is:

1. A multilayer interference pigment in the form of pigment particles consisting of a central layer of a transparent or semitransparent material of low refractive index and alternating layers of:

(a) a metal or a material of high refractive index and
   (b) a material of low refractive index, on either side of the central layer.

2. An interference pigment according to claim 1, wherein at least one material of low refractive index is $MgF_2$, a metal oxide or a polymer.

3. An interference pigment according to claim 1, wherein at least one material of low refractive index is an acrylate polymer.

4. An interference pigment according to claim 1, wherein at least one material of low refractive index is an $SiO_2$ or $Al_2O_3$ or a mixture thereof.

5. An interference pigment according to claim 1, having at least one layer of high refractive index being a metal layer of aluminum, chromium, nickel, a Ni—Cr alloy or silver.

6. An interference pigment according to claim 1, having at least one layer of a material of high refractive index being $TiO_2$, $ZrO_2$, $Fe_2O_3$, $Cr_2O_3$, ZnO or a mixture of these oxides or an iron titanate, a titanium suboxide or a mixture or mixed phase of these compounds.

7. A process for preparing an interference pigment according to claim 1, which comprises:

applying a release layer comprising a water- or solvent-soluble material to a substrate, depositing a layer system comprising the alternating layers of a material of low refractive index and of a metal or of a material of high refractive index onto the release layer, the central layer applied being a layer of a transparent or semitransparent material of low refractive index, removing the layer system from the substrate by dissolving the release layer, and washing and drying the resulting platelet-shaped interference pigment, subjecting the pigment to heat treatment at from 100 to 300° C., in a stream of nitrogen, and milling and classifying the treated pigment.

8. The process of claim 7, wherein at least one material of low refractive index is $MgF_2$, a metal oxide or a polymer.

9. A process according to claim 7, wherein at least one material of low refractive index is an acrylate polymer.

10. A process according to claim 7, wherein at least one material of low refractive index is $SiO_2$ or $Al_2O_3$ or a mixture thereof.

11. A process according to claim 7, wherein at least one layer of high refractive index is an aluminum, chromium, nickel, a Ni—Cr alloy or silver metal layer.

12. A process according to claim 7, wherein at least one layer is of a material of high refractive index which is $TiO_2$, $ZrO_2$, $Fe_2O_3$, $Cr_2O_3$, ZnO or mixtures of these oxides or an iron titanate, titanium suboxide or a mixture of mixed phase of these compounds.

13. A paint, printing ink, plastic or cosmetic composition comprising a pigment according to claim 1.

14. A composition according to claim 13, wherein the pigment is provided in admixture with at least one other pigment.

15. A method for pigmenting a paint, printing ink, plastic or cosmetic which comprising mixing therewith a pigment according to claim 1.

* * * * *